(12) United States Patent
Dall et al.

(10) Patent No.: US 8,657,857 B2
(45) Date of Patent: Feb. 25, 2014

(54) BONE FIXATION DEVICE

(75) Inventors: Vagn Erik Dall, Langley (GB); Cody Eric Bunger, Auning (DK)

(73) Assignee: Dalmatic Lystrup A/S, Lystrup (DK)

( * ) Notice: Subject to any disclaimer, the term of this patent is extended or adjusted under 35 U.S.C. 154(b) by 130 days.

(21) Appl. No.: 13/127,776

(22) PCT Filed: Nov. 5, 2009

(86) PCT No.: PCT/GB2009/002612
§ 371 (c)(1),
(2), (4) Date: Jun. 24, 2011

(87) PCT Pub. No.: WO2010/052462
PCT Pub. Date: May 14, 2010

(65) Prior Publication Data
US 2011/0245883 A1    Oct. 6, 2011

(30) Foreign Application Priority Data

Nov. 5, 2008 (GB) .................................. 0820251.7

(51) Int. Cl.
*A61B 17/70* (2006.01)

(52) U.S. Cl.
USPC .......................................... 606/268; 606/267

(58) Field of Classification Search
USPC ......... 606/53, 54–59, 60, 246, 247, 250–278, 606/300–321, 323–325, 328
See application file for complete search history.

(56) References Cited

U.S. PATENT DOCUMENTS

| | | | |
|---|---|---|---|
| 4,620,533 A * | 11/1986 | Mears ............................. | 606/54 |
| 4,771,767 A * | 9/1988 | Steffee .......................... | 606/256 |
| 5,662,651 A | 9/1997 | Tornier et al. | |
| 5,938,663 A * | 8/1999 | Petreto ........................... | 606/278 |
| 6,565,564 B2 * | 5/2003 | Hoffman et al. ............... | 606/59 |
| 6,569,164 B1 * | 5/2003 | Assaker et al. ............... | 606/250 |
| 7,585,299 B2 * | 9/2009 | Rezach ........................... | 606/60 |
| 7,648,520 B2 * | 1/2010 | Markworth .................... | 606/246 |
| 7,803,174 B2 * | 9/2010 | Denis et al. ................... | 606/250 |
| 8,147,490 B2 * | 4/2012 | Bauer ............................. | 606/57 |
| 2004/0039388 A1 * | 2/2004 | Biedermann et al. ........... | 606/71 |
| 2004/0111088 A1 * | 6/2004 | Picetti et al. .................... | 606/61 |
| 2005/0171537 A1 | 8/2005 | Mazel et al. | |
| 2005/0192572 A1 | 9/2005 | Abdelgany et al. | |
| 2007/0118121 A1 * | 5/2007 | Purcell et al. .................. | 606/61 |

(Continued)

FOREIGN PATENT DOCUMENTS

DE    19534136    3/1996
EP    1759647    3/2007

(Continued)

*Primary Examiner* — Pedro Philogene
*Assistant Examiner* — Lynnsy Schneider
(74) *Attorney, Agent, or Firm* — Woods Oviatt Gilman LLP; Katherine H. McGuire, Esq.

(57) ABSTRACT

A bone fixation device has a housing on the exposed head of a screw mounted in a bone part from which it projects. A clamp for a fixation rod is mounted on a plate extending from each of opposite lateral sides of the housing in such a manner that allows the plate to rotate about a lateral axis relative to the housing. Each clamp is itself rotatable on its plate about an axis perpendicular to its respective lateral axis, and thereby provides universal movement relative to the housing. Mechanisms are provided for closing the clamps, for locking each plate against rotation about its lateral axis, and blocking each clamp against rotation about its perpendicular axis. In this way rods can be fixed in the clamps and relative to the device.

13 Claims, 7 Drawing Sheets

(56) References Cited

U.S. PATENT DOCUMENTS

2008/0071276 A1* 3/2008 Ferree .................. 606/61
2009/0264931 A1* 10/2009 Miller et al. .................. 606/251

FOREIGN PATENT DOCUMENTS

| | | |
|---|---|---|
| EP | 1 982 663 | 10/2008 |
| FR | 2720261 | 12/1995 |
| FR | 2832620 | 5/2003 |
| JP | 11178838 | 7/1999 |
| WO | WO 95/32676 | 12/1995 |
| WO | WO 2003/037200 | 5/2003 |
| WO | WO 2006103087 A1 * | 10/2006 |
| WO | WO 2007/056709 | 5/2007 |
| WO | WO 2008/027332 | 3/2008 |

* cited by examiner

BONE FIXATION DEVICE

This invention relates to fixation systems for bones after surgery, and has particular application to the setting or controlling of bone parts. It is applicable to the fixation of bone sections after fracture, and also to the relative orientation of bone parts such as vertebra between which some movement must be permitted after spinal surgery.

Fixation devices for bone parts are known, and in this respect reference is directed to International Patent Publication No: WO 02/03868 in the name of Vagn Erik Dall, incorporated herein by reference. That specification discloses a device in which one or two bone fixation rods are mounted on a bone screw to couple that screw to a similar screw in an adjacent bone part. The fixation rods are gripped relative to a support body mounted on bone screw between jaws which close in response to pressure generated by engagement against the wall of the support body. The present invention is directed at a similar device and related fixation systems, but which offer greater flexibility and versatility.

According to one aspect of the present invention a bone fixation device comprises a screw for mounting in a bone part with an exposed head projecting therefrom. A housing on the exposed head of the screw supports a plate extending from each of two opposite sides of the housing upon which is mounted a clamp for a fixation rod. Each plate is rotatable about a lateral axis relative to the housing, and each clamp is rotatable on its plate about an axis perpendicular to its respective lateral axis. Each clamp is therefore capable of universal movement relative to the housing. The housing will normally be rotatable on the exposed head of the screw, but locked against such rotation once its preliminary orientation has been established. Mechanisms are provided for closing the clamps, for locking each plate against rotation about its lateral axis, and for locking each clamp against rotation about its perpendicular axis. Thus, once these mechanisms have been activated, rods held in the clamps are locked in position relative to the screw head.

In one preferred embodiment of the invention, each clamp has an outer jaw and a movable inner jaw on a support rotatably mounted on the respective plate. The clamp locking mechanism comprises an element within the housing for engaging the inner jaw, to move it towards the outer jaw and thereby secure a fixation rod therebetween. This engagement can also lock one or both jaws against rotation about one or both of its lateral and perpendicular axes. The engaging surfaces may be textured or otherwise treated to achieve this locking effect. They would in any event, normally be matchingly spherical to maximise the surface engagement. The element itself may be fixed within the housing, with the respective plates being movable parallel to their lateral axes. Such movement inwards urges the inner jaw against the element. This inward movement may be effected by a locking ring with an external screw thread received in a complementary internal screw thread in the housing. The locking ring can overlay an inner shoulder on the respective plate against which it engages to urge the plate inwards. Rotation of the locking ring can in this way, by urging the inner jaw of the clamp against the housing element, simultaneously lock a rod in the clamp and the clamp against rotation about both of the lateral and perpendicular axes.

In one simple form, the inner jaw of each clamp is mounted simply for pivotal movement relative to the outer jaw. Further, in order to minimise the number of moving parts, the inner and outer jaw are preferably integral parts of the same unit, and the pivotal movement is allowed by the deformation of the material used.

In another preferred embodiment of the invention the housing includes a bracket with pairs of spaced part-cylindrical surfaces on opposite lateral sides thereof on which the plates are supported for pivotal movement about the lateral axis. Each surface pair defines either side of a groove extending beneath shoulders under the respective surfaces. Each clamp is mounted on a boss extending through its respective plate to a locking element in the groove extending beneath the shoulders under the part-cylindrical surfaces. Each clamp also has jaws forming a groove for receiving a fixation rod and a clamping element over the rod. The groove depends into the boss such that a rod received in the groove engages the plate at either end of the groove. Activation of the clamping element locks the rod and clamp relative to the plate and the plate relative to the bracket to prevent any movement of the rod relative to the head of the screw. Each locking element can be integral with its respective clamp boss, but this requires the plate to be formed with a slot to enable the device to be assembled. Preferably, the element is separate, and attached to the clamp boss for example, by means of a bayonet coupling. A friction pad can be disposed between the locking element and the shoulders under the respective part-cylindrical surfaces, to assist the locking process.

A bone fixation device according to another aspect of the invention comprises a screw for mounting in a bone part with an exposed head projecting from the bone. A housing on the exposed head of the screw has jaws defining adjacent grooves for receiving fixation rods. Each groove has a central section in which the base has a part-spherical surface and opposed end sections in which the base has a surface divergent from the central section base. In each groove is a split ball element with a diametral bore therethrough; and a clamping element for compressing each ball element, contracting the bore therethrough, and clamping the element against said part-spherical surface.

The diametral bore through at least one split ball element can be sized to receive, contract around and clampingly engage a fixation rod, or receive, contract around and clampingly engage a sleeve for slidingly receiving at least one fixation rod.

Fixation devices of the invention are useful in many aspects of surgery, and are very effective when bone parts must be fixed relative to one another. A pair of fixation rods can extend between adjacent devices, to provide a very stable locking mechanism. At the same time, it will be appreciated that prior to the clamps and plates being locked, the loosely assembled structure of screws, fixation rods and bone parts can be manoeuvred into precise position. Once that position has been found, a single movement of each locking ring in the preferred embodiment can set the assembly.

The present invention also has application in surgery where bone parts must be located relative to one another, but in a manner which allows for controlled relative movement. This is particular important after spinal surgery on a young patient who is still growing. For example, in a child treated for scoliosis a surgeon will want to set adjacent vertebra in such a manner that permits them to grow apart, but in a predetermined direction. In other words, the relative movement of the vertebra should be restricted to one which counteracts the deformity. This can be achieved in a fixation system in which fixation rods held in mounts on each of adjacent vertebra are coupled in a sleeve which allows the mounts (and therefore the vertebra) to separate, but only in a direction determined by the fixation rods and the respective sleeve or sleeves. Such a system is described in our co-pending International Patent Application entitled "Bone Fixation System" claiming priority from British Patent Application No: 0820252.5, incorporated by reference. Generally, the end of one rod will be fixed in an end of the sleeve with the juxtaposed end of the other rod slidably received in the other end of the sleeve. The extent of movement of the other rod will normally be restricted to retain at least a minimum end length of each rod in the sleeve, and this can be accomplished by the end of the movable rod being formed with a longitudinal groove extending axially on its surface, but terminating short of the rod end. A spigot in the sleeve is received in the groove. The spigot is typically the end of a screw installed from the exterior of the sleeve, and therefore withdrawable to allow for initial insertion of the rod in the sleeve.

A single rod and sleeve combination extending between mounts in adjacent vertebra provides some control over their relative movement, but it is preferred to use two such combinations side by side. The respective rods can be fixed in separate mounts on the vertebra, or on opposite sides of a housing on the exposed head of a bone screw, using a device of the kind described above. The use of two rods side by side does of course provide a much more stable and controlled link between the adjacent bone parts.

If the permitted movement of adjacent bone parts using such a fixation system is to be linear, then the fixation rod and sleeve combination or preferably combinations will be straight. However, and particularly in surgery to combat scoliosis, the permitted movement may need to be along a curved path. This can be accomplished by selecting a rod or rods with appropriate curvature, and matching that curvature with a correspondingly curved sleeve, as necessary. Different circumstances will of course require different kinds and degrees of curvature, and different geometric figurations can be achieved by selecting appropriate rods and sleeves, and the respective orientations of the rods when they are fixed in the mounts in the respective bone parts.

The fixation rods themselves will normally be of circular cross-section, but there may be situations in which a polygonal cross-section might have benefits. A polygonal cross-section of the rod and the sleeve interior will of course prevent rotation of one relative to the other. This can be additional to the use of the spigot and groove referred to above which does of course serve a similar purpose but can lock if a substantial twisting force is applied to a rod.

As a further mechanism for stabilising relative movement of adjacent bone parts in a fixation system of the invention, the sleeves in which adjacent rods are received can be coupled together. This provides some additional resistance to adjacent vertebra twisting relative to one another.

The invention will now be described by way of example and with reference to the accompanying illustrative drawings wherein.

Figure 1:
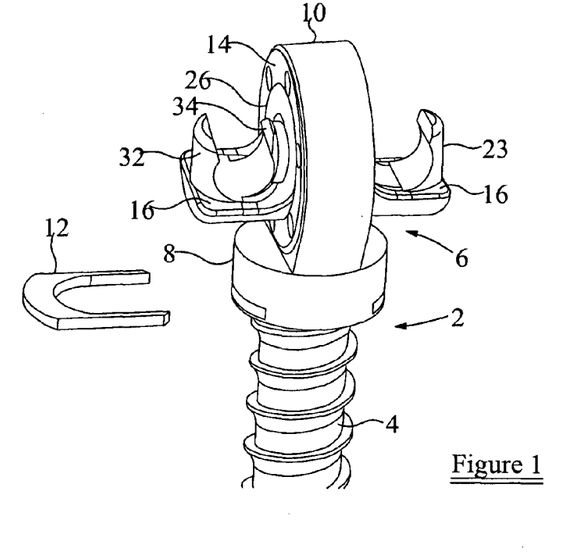
FIG. 1 is a perspective view of a bone fixation device according to a first embodiment of the invention.

FIG. 1 shows the head 2 of a bone screw 4 as it might project from a bone (not shown) after installation during surgery. On the head is mounted a housing 6 comprising a base 8 and a drum 10. The base 8 will normally be formed with a frusto conical recess which received the head 2 of the screw 4. This initially allows rotation of the base on the head, but once this is set in a desired orientation, it is locked by installation of a circlip 12.

Figure 2:
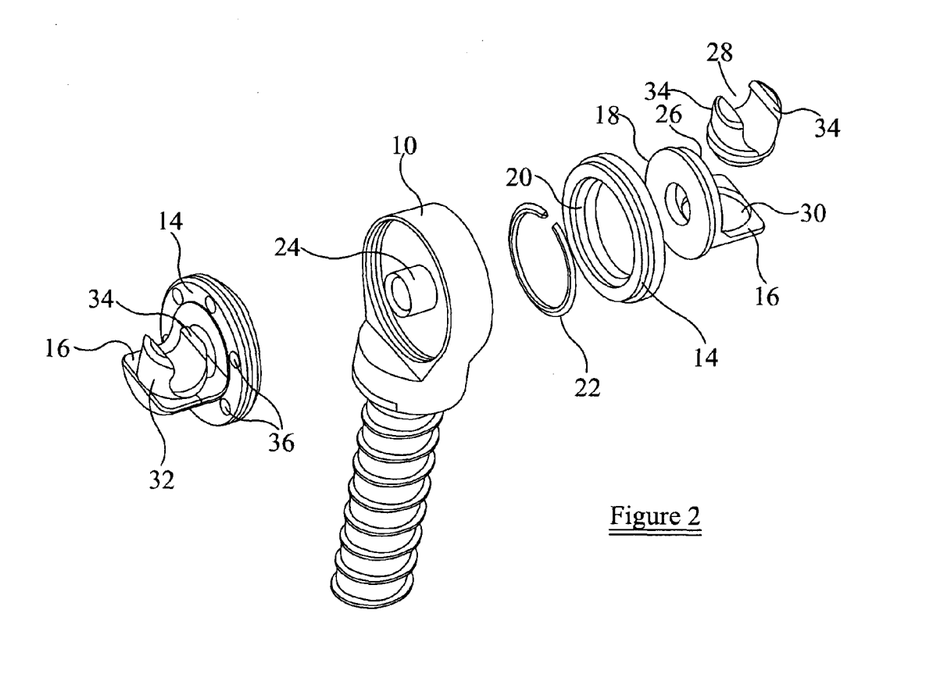
FIG. 2 is a part exploded view of the device of FIG. 1.

As shown in FIG. 2, the drum 10 is formed with two threaded recesses (only one is shown) facing in opposite directions. When assembled, a locking ring 14 holds a plate assembly 16 in the recess by virtue of an annular projection 18 from the base of each plate 16 engaging an annular shoulder 20 within the respective locking ring. A split ring 22 (only one is shown) holds the annular projection 18 and shoulder 20 in engagement during assembly of the device as a whole, and until the locking ring is tightened.

The locking rings 14 are axially aligned around two cylindrical projections that also extend through the boss sections 26 of the plates 16 and define lateral axes along which the plates 16 can move. The distal end surface of the wall of each projection 14 has a concave spherical surface for reasons which are described below.

Each plate 16 carries a clamp unit 28 which has a circular base received in a circular recess in the plate. This provides for rotation of each clamp unit 28 about an axis perpendicular to the common lateral axis of the plates 16. The circular base of the clamp unit will be held in the plate recess 30 by means of a resilient circlip (not shown).

Each clamp unit has an outer jaw 32 and an inner jaw 34. The clamp unit itself is an integral body, and the movement of the jaws towards and away from each other is as a consequence of the resilient flexure of the material of the clamp and particularly of the inner jaw 34. As can be seen, each inner jaw is formed as a section extending from the outer jaw, and its mass and dimensions are generally less than those of the outer jaw to facilitate such relative movement. The outer face of each inner jaw has a convex spherical shape and is in juxtaposition with the distal end of the respective projection 24. The respective spherical surfaces match, such that there is uniform contact between them when they engage.

When the device is assembled, each locking ring 14 may be rotated in its respective drum recess, the threads causing the ring to drive the respective plate inwards by virtue of engagement between the annular projection 18 on each plate, and the shoulder 20 on each locking ring. This movement causes the end face of the projections 24 to engage the convex face of the movable jaw 34 serving simultaneously to close the clamp unit 28, and lock it against rotation about either the lateral axis of the plate, or the perpendicular axis of the clamp unit. The engaging faces of the projection 24 and the movable jaw 34 may be knurled or otherwise roughened or treated to enhance the locking effect. Additional locking may be established by friction between the inner end face of each locking ring 14 and the base of the respective drum recess, by means of a resilient washer therebetween.

The flexibility of the inner jaw 34 in each clamp unit 28 facilitates the initial insertion of fixation rods and once a rod is installed the device may be locked as described above, in a relatively swift and often single movement. A key can be provided for engaging openings 36 in each locking ring 14 to enable such locking to be quickly and effectively accomplished.

Figure 3:
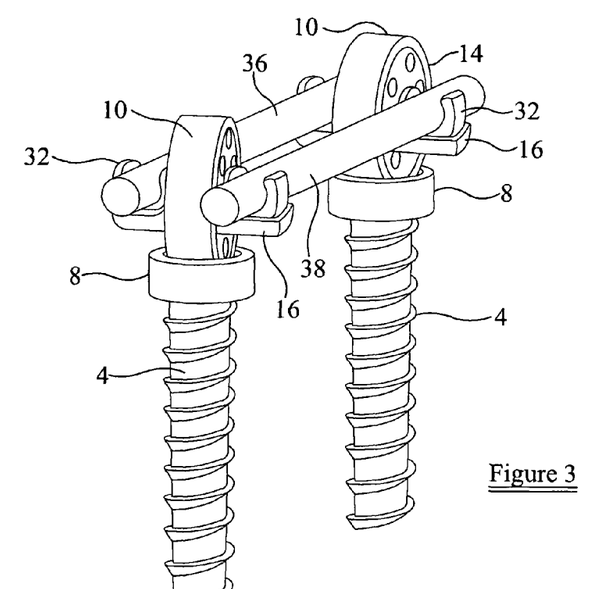
FIG. 3 illustrates two devices of the invention with fixation rods extending therebetween.

FIG. 3 shows how two fixation rods can be installed to extend between two devices of the kind illustrated in FIGS. 1 and 2, and it will be noted that the drums 10 of the respective devices are not aligned in a common plane. This illustrates how the respective devices can be manoeuvred to ensure that the various locking mechanisms can be secured.

Figure 4:
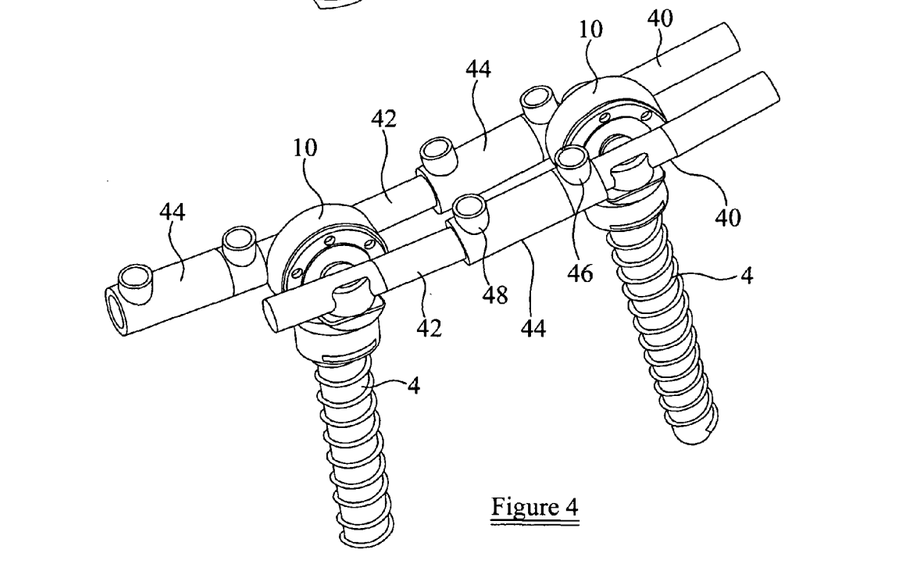
FIG. 4 is a perspective view illustrating a second embodiment of the invention.

FIG. 4 illustrates a second embodiment of the invention. Specifically, it shows how two fixation rods 40 and 42 can be mounted in alignment in two fixation devices of the kind described above, and interconnected by a sleeve 44. The rod 40 is fixed in the sleeve 44 by a clamping screw (now shown) in the bell 46. The rod 42 is slidably received in the other end of the sleeve 44. This construction enables the respective fixation devices to be installed in adjacent vertebra for example, but in a manner which allows the vertebra to grow apart without restriction by the fixation system. However, as damage is likely to be caused if the rod 42 were to exit the sleeve 44, its outward movement is restricted by an inwardly directed screw or spigot mounted in bell 48 that extends into a groove or similar (not shown) in the rod 42 which terminates before its end within the sleeve 44. The diameter of the fixation rods used in devices and systems of the invention will normally be around 4 mm. The depth to which the rod ends are inserted and retained in the cylinders will normally be controlled to be at least equal to the rod diameter.

FIG. 4 shows rods extending on both sides of drums 10 mounted on screws 4 inserted or to be inserted in adjacent bone parts. It will though, be appreciated that there may well be circumstances in which only a single rod is required to be mounted on each screw 4. In those circumstances of course, it is not necessary to use a fixation device of the kind illustrated in FIGS. 1 to 3. A single rod mounting device, for example of the kind illustrated in FIG. 1 of International Publication No: WO 02/03868, incorporated by reference, or similar, may be used. Generally though, it is preferred to use aligned rods in parallel, for the reasons set out below.

Figure 5:
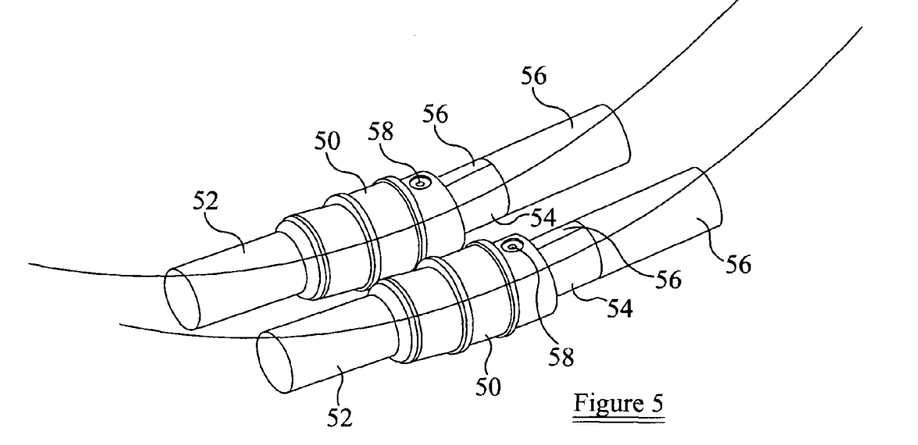
FIG. 5 illustrates a variation on the embodiment of FIG. 4.

FIG. 5 shows an alternative sleeve and rod assembly. In this embodiment, each sleeve is integral with one fixation rod section 52 to be clamped in a fixation device, for example of the kind illustrated in FIGS. 1 and 2. The other end of each sleeve 50 receives a curved section 54 of the other fixation rod, which merges with a straight section 56 for clamping in a fixation device installed in an adjacent bone part such as another vertebra. The curved section 54 is formed with a groove 56 on its surface aligned with its axis. A screw 58 driven through the wall of the sleeve 50 extends into the groove 56. The groove stops short of the end of the rod within the sleeve to prevent it from withdrawing entirely from the sleeve. The engagement of the screw and groove also of course inhibits rotation of the rod relative to the sleeve. The interior of the sleeve which receives the rod section 54 is curved in the same sense. Thus, as the rod 54 is withdrawn from the sleeve as the attached bone parts (vertebra) separate, such separation is constrained to be along the line of the curve, as indicated. With two sleeves and respective rod sections, the curves are matched, and as a consequence the aligned rod sections define what is effectively a curved plane in which the adjacent bone parts are constrained.

Figure 6:
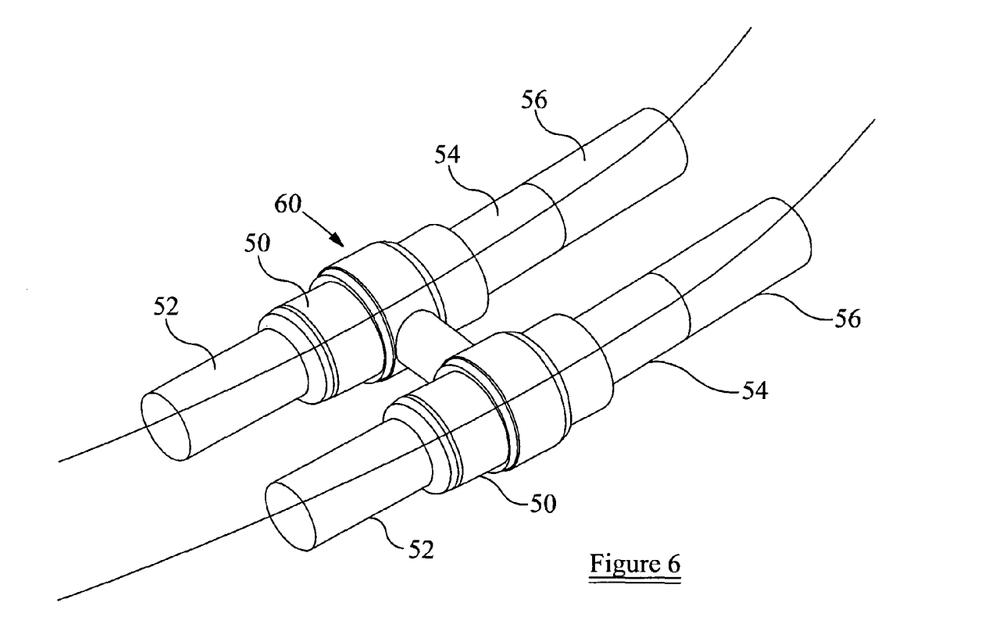
FIG. 6 illustrates a further variation on the embodiment of FIG. 4.

FIG. 6 illustrates a similar arrangement to that of FIG. 5, but here the two sleeves are coupled together to provide greater stability as the rod sections 54 are withdrawn from the sleeves 50. The coupling unit 60 preserves the spacing between the sleeves, and any relative rotation. Where relatively large amount of movement must be accommodated between coupled bone parts, this additional control can be very valuable.

Figure 7:
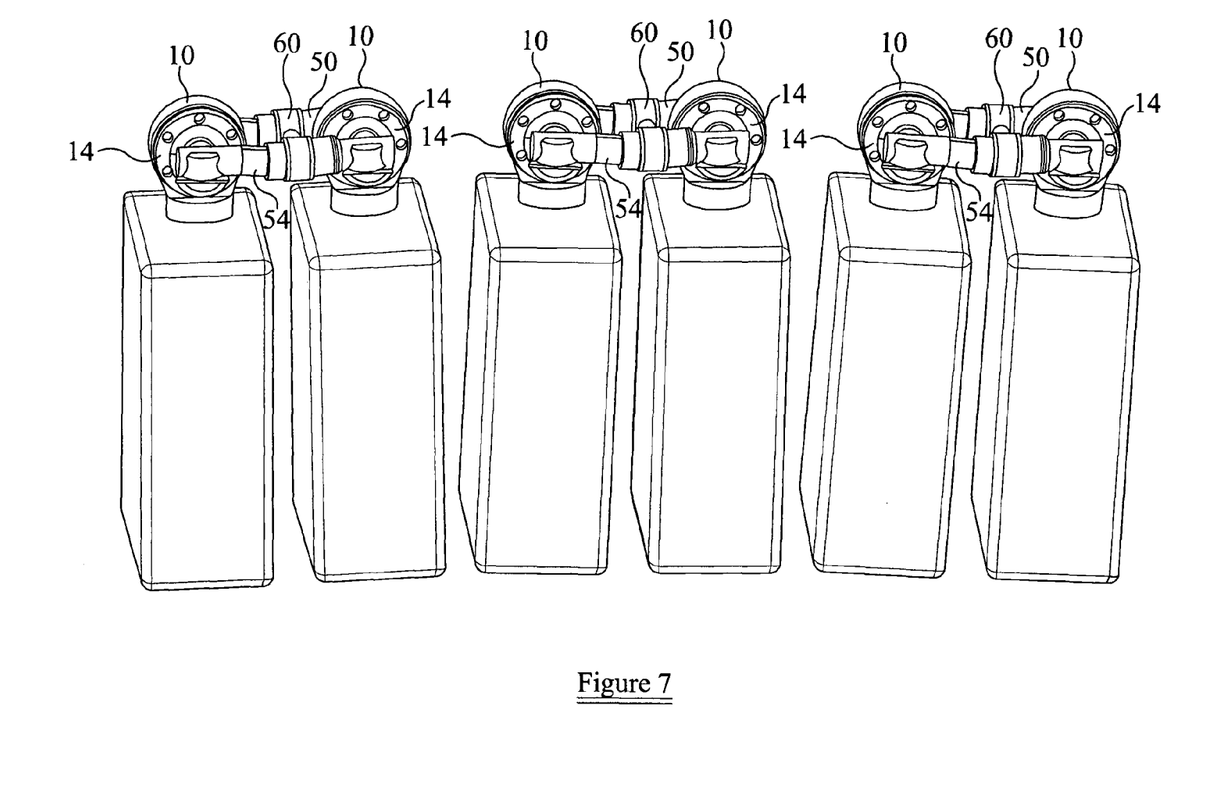
FIG. 7 illustrates schematically how the embodiment of FIG. 6 can be applied in the treatment of spinal deformations.

FIG. 7 illustrates how fixation systems of the invention can be used after spinal surgery to control the alignment of adjacent vertebra while permitting them to grow apart. The vertebra are illustrated as rectanguloid blocks and as can be seen, each fixation system constrains the respective interconnected vertebra to move out of alignment as they grow apart. This serves to move adjacent vertebra, between which no fixation system is installed, to move out of alignment in the opposite sense, but in practice as a spine grows and develops the result will be that the vertebra grow in substantial alignment. It will be appreciated of course, that the degree of curvature in the rods and sleeves has to be selected with great care in order to achieve the desired result.

Figure 8:
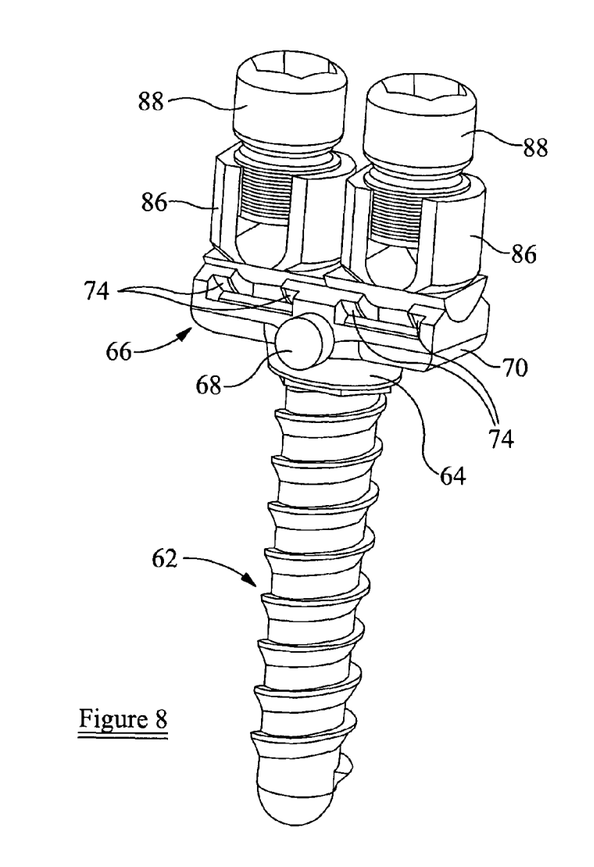
FIG. 8 is a perspective view of a bone fixation device according to a second embodiment of the invention.

FIG. 8 illustrates a device according to the invention which operates in a manner similar to that shown in FIG. 1, in that a rod is held in each of two clamps on the screw, each clamp being allowed to pivot until the orientation of the rod and clamp are secured. In a manner similar to the device of FIG. 1, a housing 66 is mounted on a head 64 of a bone screw 62. In the embodiment of FIG. 8, the housing is secured on the head 64 by means of a locking pin 68. The housing itself comprises a bracket 70 on which are formed pairs of spaced part-cylindrical surfaces 72. These surface pairs define opposite sides of grooves extending beneath shoulders 74 which extend under the respective surfaces 72.

Plates 76 are formed with part-cylindrical lower surfaces which complement and rest on the surfaces 72. Each plate can therefore pivot about a lateral axis defined by the common axis of the respective cylindrical surfaces. Of course, it is not essential that both plates pivot about the same axis, but in practice this will almost always be the case.

Supported on the respective plates 76 are clamps 78. Each clamp has a boss 80 which extends through an opening in its respective plate 76 and into the groove defined under and between the surfaces 72. There it is attached to a locking element 82 which extends laterally under the shoulders 74. Interposed between its locking element 82 and the respective shoulders 74 is a friction pad 84 to assist the locking process.

Each clamp has two jaws 86 defining a groove for receiving a fixation rod (not shown). A clamping element 88 in the form of a screw with an Allen Key socket engages a complementary screw thread defined on the internal faces of the jaws 86.

Figure 9:
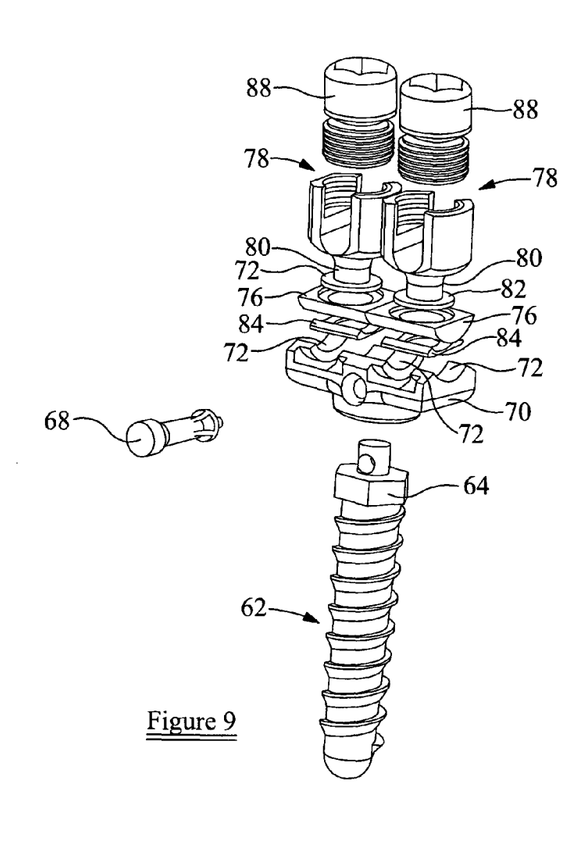
FIG. 9 is an exploded view of the device of FIG. 8.

As can be seen in FIG. 9, the holes in the plates 76 through which the bosses 80 extend have a chamfered perimeter. This enables the groove defined between the jaws 86 of each clamp to extend below the surface of the plate when the device is assembled. As a consequence, when a fixation rod is fitted in a groove, and the clamping element 88 driven downwards to engage it, the rod itself is forced not against the base of the groove, but against the upper surface of a plate 76. Thus, when the clamping element is tightened, the rod is locked in the groove; the clamp 86 is locked in the plate 76; and the plate 76 is locked against the surfaces 72 of the bracket 70 as the locking element 82 is drawn against the friction pad 84 and the shoulders 74. As with the device of FIG. 1 then, a single locking action secures a fixation rod against axial movement in the groove, and pivotal movement in any direction.

Figure 10:
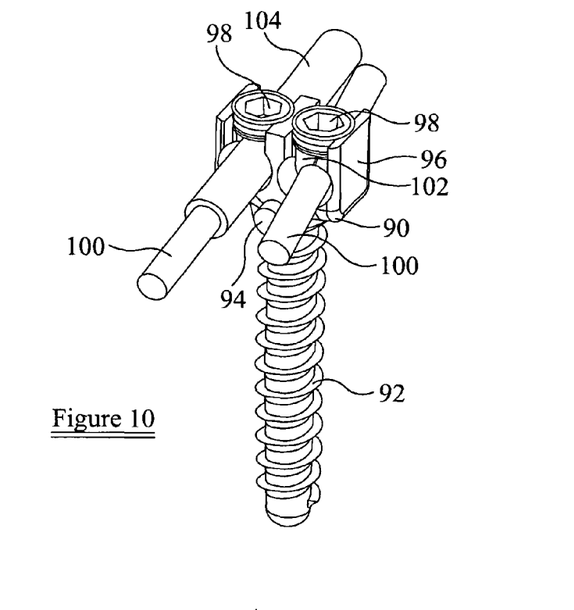
FIG. 10 is a perspective view of a bone fixation device according to a third embodiment of the invention.

FIG. 10 illustrates a bone fixation device according to a third embodiment of the invention. As with the embodiments of FIGS. 1 and 8, two separately lockable clamps are defined as part of a housing 90 mounted on the head of a bone screw 92, secured by means of a locking pin 94. However, in the embodiment of FIG. 10 the clamps are defined side-by-side in a unitary body 96. Each clamp has a locking element 98 similar to element 88 in FIG. 8, in the form of a screw engaging a complementary screw thread defined on the juxtaposed sides of a groove for receiving a fixation rod 100. However, in the embodiment of FIG. 10 the fixation rod passes through a split ball element 102 having an external spherical surface which rests in an internal spherical surface at a central section of the groove over which the locking element 98 is disposed. When the locking element is driven into the groove, it compresses the ball element to contract the bore therein through which the fixation rod extends, locking the rod in the ball element and the ball element in the groove.

While the clamping element 98 is disengaged or only loosely engaged with the ball element 102, the ball element can pivot in the groove within the central spherical surface. The end sections of the groove diverge from the central section to allow a rod 100 fitted in the ball element 102 limited pivotal movement also about the centre of the ball element 102. The base of each groove end section preferably has a frusto-conical surface extending around more than 180°, for reasons that will become apparent.

The above description of the installation of a fixation rod is described above with reference to the clamp shown on the righthand side in the device of FIG. 10. The clamp on the lefthand side of the device shown in FIG. 10 is essentially similar, but the bore through the ball element 102 is larger. This enables it to receive a sleeve 104, which has limited pivotal movement while the clamping element is disengaged, but can be locked in a similar way when the element is engaged. However, the fixation rod 100 is locked in orientation, but can still move axially within the sleeve. The reason for this is explained below.

Figure 11:
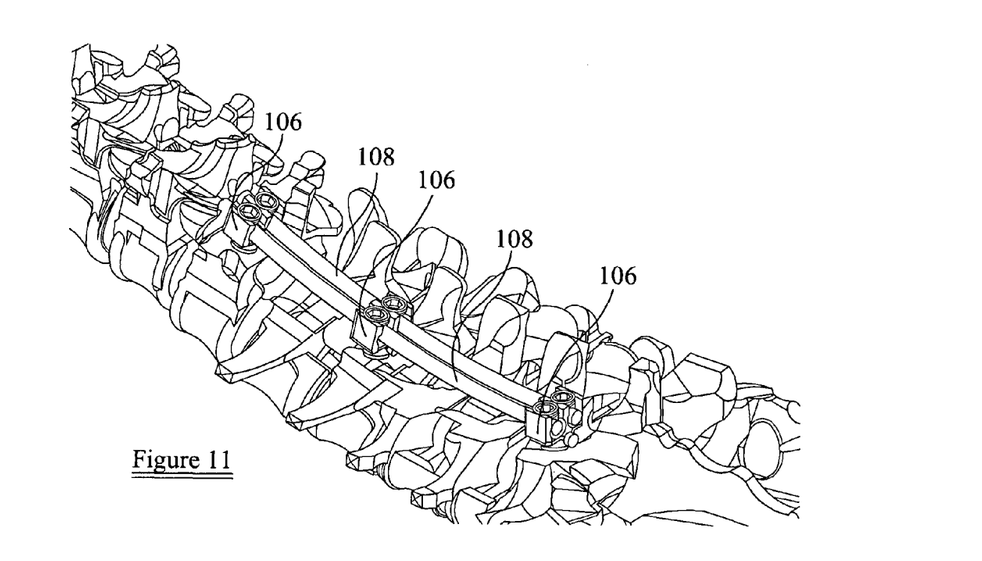
FIG. 11 illustrates schematically how devices of the kind shown in FIG. 10 can be applied in the treatment of spinal deformations.

FIG. 11 illustrates how fixation devices according to the invention can be used in spinal surgery. Three devices 106 are shown, mounted on alternate vertebra with a pair of fixation rods 108. Each rod 108 is secured by a clamp in each of the three devices 106. As shown therefore, the devices and rods secure the alignment of the vertebra to which the devices are attached, and thereby the vertebra in between. The primary purpose of a fixation system of the kind illustrated in FIG. 11 is to reinforce the spine and prevent undue curvature.

Figure 12:
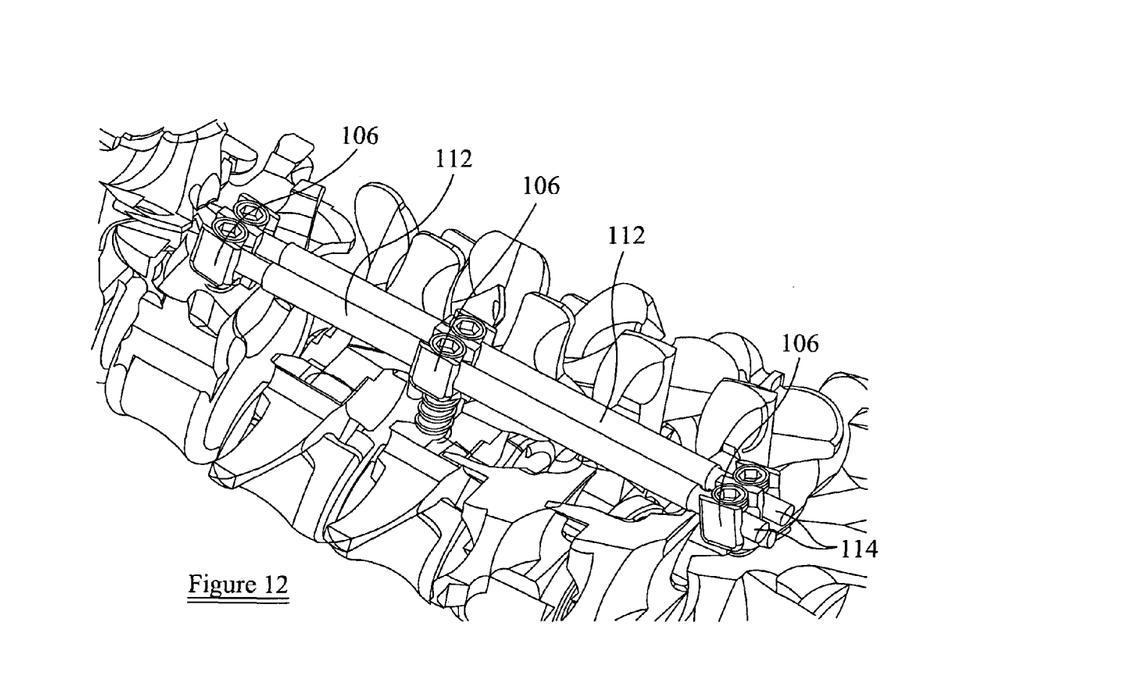
FIG. 12 shows a view similar to that of FIG. 11 in which spinal growth is accommodated.

FIG. 12 illustrates a fixation system that serves an additional purpose. In the system of FIG. 12, three devices are once again installed on alternate vertebra, but device 110 installed on the central vertebra clamps not fixation rods 108, but sleeves 112. Rods 114 are not continuous between the devices 106, but are discontinuous. This enables the spine to grow; ie, the vertebra on which the devices 106 are mounted can move away from each other during normal growth, while the rods and sleeves preserve the orientation and alignment of the vertebra to which the devices 106 and 110 are attached, and the intervening vertebra therebetween.

It will be appreciated that the fixation devices shown in FIGS. 11 and 12 could be any of the embodiments described above, as each provides the flexibility needed to accommodate rods and sleeves at the required orientation. It will be appreciated therefore, that while the mounting of a sleeve in a fixation device is only described with reference to the embodiment of FIG. 10, the devices of FIGS. 1 and 8 can be readily adapted to perform the same function.

Figure 13:
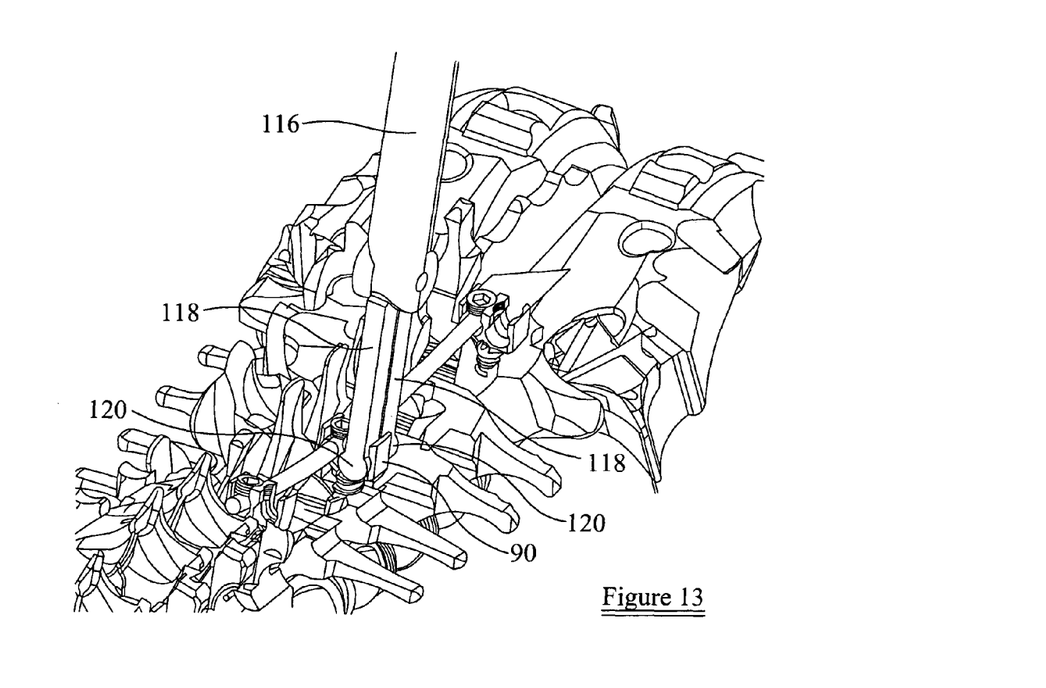
FIG. 13 illustrates how a tool can be coupled to a device of the kind shown in FIG. 10 after installation on a vertebra to manipulate a vertebra during the course of an operation.

In the conduct of delicate spinal surgery, it is often necessary to manipulate individual vertebra in the spine before fitting a fixation system of the kind described above. Such manipulation has to be conducted with great care and accuracy. This is not always possible when using a surgeon's hand. Devices of the present invention provide a very convenient means by which an individual vertebra on which a device has been installed, can be manipulated with minimal direct contact between the surgeon's hands and the spine under surgery. In the embodiment of FIG. 1, the drum 10 of the housing 6 can be grasped either directly by the surgeon or remotely by a gripping device. In the devices of FIGS. 8 and 10 one of the clamping elements (88,98) can be removed and a manipulator probe having a suitably threaded end installed in one of the clamps. The embodiment of FIG. 10 provides a particularly convenient alternative to these techniques. As shown in FIG. 13, a manipulator tool 116 having two pivotal arms 118 can lock onto the housing 90 by means of conical elements 120 at the distal ends of the arms engaging the frusto-conical surfaces of the end sections of one of the grooves. This technique has the advantage that the distal ends of the arms can be swiftly engaged or disengaged, and the length of the tool can enable manipulation to be conducted from a distance with a maximum amount of the vertebra being manipulated and adjacent vertebra, being in view.

Devices and systems of the invention will normally be formed in titanium or, stainless steel or some other material which can be safely used in surgical applications. The use of resilient synthetic materials is best avoided, and for this reason the components must be manufactured with considerable precision.

The invention claimed is:

1. A bone fixation device comprising a screw for mounting in a bone part with an exposed head projecting from the bone; a housing on the head of the screw with a clamp for a fixation rod mounted on a plate extending from each of opposite lateral sides of the housing, each plate being rotatable about a lateral axis relative to the housing and having a support surface extending in a plane parallel to the lateral axis, and each clamp being rotatable on a respective support surface about an axis perpendicular to the lateral axis to provide universal movement relative to the housing; and mechanisms for closing the clamps, for locking each plate against rotation about its lateral axis, and for locking each clamp against rotation about its perpendicular axis, and thereby fix rods in the clamps relative to the device, wherein each clamp has an outer jaw and a movable inner jaw, and wherein the locking mechanism for each clamp comprises an element of the housing for engaging the inner jaw to move it towards the outer jaw and secure a fixation rod therebetween.

2. A bone fixation device according to claim 1 wherein the housing is mounted for rotation on the head of the screw.

3. A bone fixation device according to claim 2 including a mechanism for locking the housing against said rotation.

4. A bone fixation device according to claim 1 wherein the clamp locking mechanism includes a locking ring in the housing, rotation of which engages the element with the inner jaw of each clamp and urges it towards the respective outer jaw.

5. A bone fixation device according to claim 4 wherein rotation of the locking ring locks the respective plate against rotation about its lateral axis.

6. A bone fixation device according to claim 1 wherein each inner jaw is adapted for pivotal movement towards the outer jaw.

7. A bone fixation device according to claim 1 wherein the surfaces of the element and the inner jaws adapted to engage are complementary spherical surfaces in juxtaposition, and wherein their engagement serves to lock the respective plate against rotation about its lateral axis.

8. A bone fixation device according to claim 1 wherein the outer jaw is movable towards said element to engage the element with the inner jaw.

9. A bone fixation device according to claim 8 including a locking ring rotatable to lock each respective plate against rotation about its lateral axis.

10. A bone fixation device comprising a screw for mounting in a bone part with an exposed head projecting from the bone; a housing on the head of the screw with a clamp for a fixation rod mounted on a plate extending from each of opposite lateral sides of the housing, each plate being rotatable about a lateral axis relative to the housing and each clamp being rotatable on its plate about an axis perpendicular to its respective lateral axis to provide universal movement relative to the housing; and mechanisms for closing the clamps, for locking each plate against rotation about its lateral axis, and for locking each clamp against rotation about its perpendicular axis, and thereby fix rods in the clamps relative to the device wherein the housing includes a bracket with pairs of spaced part-cylindrical surfaces on opposite lateral sides thereof on which the plates are supported for pivotal movement about said lateral axes, each of which surface pair defines either side of a groove extending beneath shoulders under the respective surfaces; wherein each clamp is mounted on a boss extending through its respective plate to a locking element in the groove extending beneath the shoulders under the part-cylindrical surfaces, and has jaws forming a groove for receiving a said fixation rod; and wherein the clamp locking mechanism includes a clamping element over the rod, the groove depending into the boss such that a rod received in the groove engages the plate at either end of the groove, activation of the clamping element locking the rod and clamp relative to the plate and the plate relative to the bracket to prevent any movement of the rod relative to the head of the screw.

11. A bone fixation device according to claim 10 wherein the locking element is attached to the clamp boss by means of a bayonet coupling.

12. A bone fixation device according to claim 10 including a friction pad between the locking element and the shoulders under the respective part-cylindrical surfaces.

13. A bone fixation device according to claim 10 wherein each clamping element is a screw with complementary female threads formed in the juxtaposed jaw faces.

* * * * *